United States Patent
Yang

(10) Patent No.: US 9,014,795 B1
(45) Date of Patent: Apr. 21, 2015

(54) SYSTEMS AND METHODS FOR DETERMINING A CARDIOVASCULAR CONDITION OF A SUBJECT

(71) Applicant: Hui Yang, Tampa, FL (US)

(72) Inventor: Hui Yang, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/036,776

(22) Filed: Sep. 25, 2013

Related U.S. Application Data

(60) Provisional application No. 61/705,395, filed on Sep. 25, 2012.

(51) Int. Cl.
*A61B 5/04* (2006.01)
*A61B 5/0408* (2006.01)
*A61B 5/00* (2006.01)

(52) U.S. Cl.
CPC ............. *A61B 5/0408* (2013.01); *A61B 5/6804* (2013.01)

(58) Field of Classification Search
USPC ................................................. 600/382, 523
See application file for complete search history.

(56) References Cited

U.S. PATENT DOCUMENTS

2008/0161671 A1* 7/2008 Voth et al. ..................... 600/382

OTHER PUBLICATIONS

Park, et al. "Enhancing the Quality of Life Through Wearable Technolgy", IEEE Engineering in Medicine and Biology Magazine, May/Jun. 2003.
Rudy, et al. "Noninvasive Electrocardiographic Imaging", Cardiac Biolelectricity Research and Training Center (CBTRC), Case Western Reserve University; vol. 4, Issue 3, Jul. 1999.
Park, "Smart Textile-Based Wearable Biomedical Systems: A Transition Plan for Research to Reality", IEEE Transactions on Information Technology in Biomedicine, vol. 14, No. 1, Jan. 2010.

* cited by examiner

*Primary Examiner* — Nicole F Lavert
(74) *Attorney, Agent, or Firm* — Thomas | Horstemeyer, LLP

(57) ABSTRACT

In one embodiment, a cardiovascular condition of a subject is determined by capturing a three-dimensional electrocardiography image of the subject, generating a two-dimensional cardiac map from the electrocardiography image, and processing the cardiac map to determine the cardiovascular condition of the subject.

17 Claims, 8 Drawing Sheets

SYSTEMS AND METHODS FOR DETERMINING A CARDIOVASCULAR CONDITION OF A SUBJECT

CROSS-REFERENCE TO RELATED APPLICATION(S)

This application claims priority to U.S. Provisional Application Ser. No. 61/705,395, filed Sep. 25, 2012, which is hereby incorporated by reference herein in its entirety.

STATEMENT REGARDING FEDERALLY SPONSORED RESEARCH OR DEVELOPMENT

This invention was made with government support under 1266331 awarded by National Science Foundation. The government has certain rights in the invention.

BACKGROUND

Heart disease is the number one cause of death in the world. Cardiac events often occur in daily life and account for some 30% of mortalities in the U.S. Unfortunately, current medical technologies and procedures typically fail to prevent life-threatening acute cardiac events (e.g., heart attacks). This is because current technologies and procedures typically do not detect the risk precursors that can lead to such an event.

Two broad categories of tests are used in clinical practice to detect cardiac disorders, namely, "static" and "dynamic" tests. Static tests are essentially frozen snapshots of cardiac information, such as x-rays, computer images, and blood enzyme test results. This sort of testing is expensive and not always readily available. Dynamic tests are those that continuously monitor heart dynamics, such as when recording electrocardiograms (ECGs). There is an increasing appreciation for the benefits of continuously monitoring the dynamic details of cardiac functioning. If such monitoring were performed on an ongoing basis, for example, several times a day, each day, cardiac disorders could be detected earlier and acute cardiac events could be avoided. However, real-time ECG monitoring generates enormous amounts of data that are simply too large for humans to visually analyze.

Another limitation of current dynamic testing is that it generates relatively low-resolution information as to cardiac activity. Recent developments in electrocardiogram imaging (ECGI) promise to provide higher resolution sensing of cardiac electrical dynamics. Moreover, ECGI has been shown to substantially enhance the detection of certain cardiac disorders in their early stages. If ECGI could be continually performed and the collected data continually analyzed, physicians would have an unprecedented opportunity to observe high-risk subjects for cardiac disorders.

Recently, sensor-embedded "smart shirts" have been developed to monitor cardiac activity. Some smart shirts that include ECG electrodes have been proposed to collect a limited number of channels of ECG signals (i.e., <12 leads). Further, an ECGI system has been proposed to include hundreds of small electrodes, but not in the form of smart shirt. Although the electrodes can be successfully used to collect ECGI data, each electrode must maintain strict contact with the skin surface, typically requiring the use of sticky gels, connectors, and/or hard plastic chest straps. As a result, such shirts are uncomfortable to wear and therefore create patient compliance issues. Furthermore, the compact representation and interpretation of large spatiotemporal data from ECGI, which is essential for a functional cyber-physical infrastructure, has not been developed.

The above-described issues pose critical scientific and technological barriers for improving the outcomes of cardiac care services. It can therefore be appreciated that it would be desirable to have a wearable ECGI system and method that could be used to monitor patients and detect cardiac disorders that pose a significant health risk to patients.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have an electrocardiogram imaging (ECGI) system and method that could be used to monitor patients and detect cardiac disorders. Disclosed herein are examples of such systems and methods. In one embodiment, a smart shirt having many electrodes and a relaxed fit is used to measure electrical potentials from many spatial locations on a patient's torso over predetermined periods of time. Three-dimensional ECGIs can be generated from the electrical potentials, and spatiotemporal reconstruction can be performed to fill in the blanks created when electrodes lose contact with the skin because of the relaxed fit of the shirt. The ECGIs can then be computer analyzed to detect the presence of a cardiac disorder. In some embodiments, this can be achieved by first transforming the three-dimensional ECG images into two-dimensional cardiac maps using a cardiac cartography process.

In the following disclosure, various specific embodiments are described. It is to be understood that those embodiments are example implementations of the disclosed inventions and that alternative embodiments are possible. All such embodiments are intended to fall within the scope of this disclosure.

Recording ECG Images of a Subject

Figure 1:
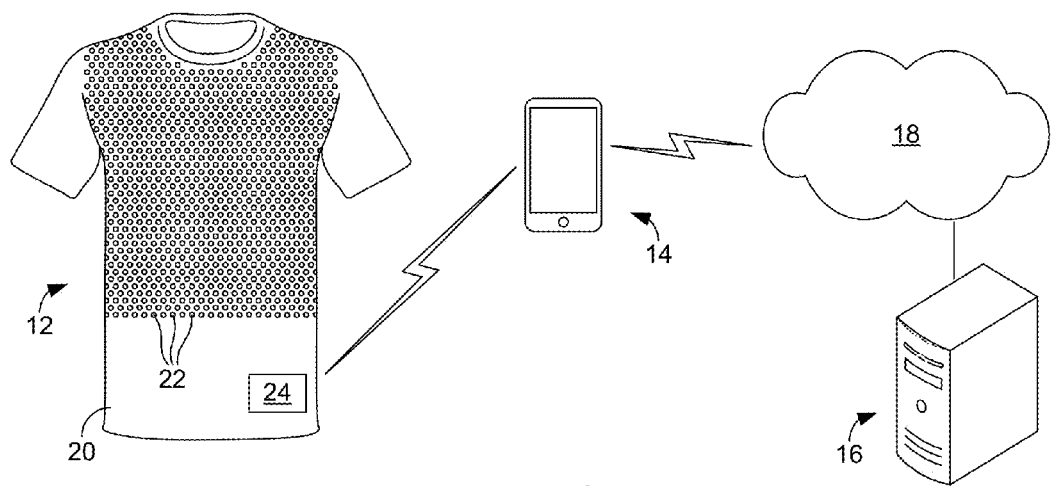
FIG. 1 is a schematic diagram of an embodiment of an electrocardiogram imaging (ECGI) system.

FIG. 1 illustrates an example ECGI system 10 that can be used to generate ECG images and detect cardiac disorders from the images. As shown in this figure, the system 10 generally comprises a smart shirt 12, a local personal computing device 14, and a remote computer 16 that can receive data from the personal computing device via a network 18.

The smart shirt 12 generally comprises a shirt substrate 20 made of a flexible fabric to which are attached (e.g., embedded) many small electrodes 22 that can contact the skin surface of a patient's torso when the shirt is worn. The shirt substrate 20 can be made of natural and/or manmade fibers. In some embodiments, the shirt 12 has a relaxed fit and is comfortable when worn so as to increase the likelihood that a patient will wear the shirt and that valuable cardiac data will be collected.

By way of example, the shirt 12 can comprise hundreds of electrodes 22 that surround the torso so that a high-resolution image of cardiac activity can be obtained from all sides of the heart. To increase wearer comfort, the electrodes 22 can comprise soft nano-textile ECG sensors that are knitted into the shirt substrate 20. Irrespective of their construction, the electrodes 22 are communicatively coupled to an integrated data acquisition device 24 that is configured to collect signals (i.e., the measured electrical potentials) from the electrodes and transmit them to the personal computing device 14. The location of the electrodes 22 can be optimized to enable reconstruction of a complete picture of underlying cardiac electrical dynamics. In some embodiments, nonlinear regression models can be wrapped into an objective function to search the space of all lead subsets to optimize the signal information. Starting from an empty lead set, the additional lead $L^+$ that maximizes the objective function $J(L_k+L^+)$ can be sequentially added into a lead subset $L_k$ that has already been selected. These steps can be repeated until the optimal signal information is obtained.

In some embodiments, signals can be collected from the electrodes 22 for a time period of one or more seconds at a sample rate of approximately 1 to 2 kHz. Assuming that the patient wears the shirt 12 all day, signals can be collected in this manner several times each day, such as every few hours. Each time signals are collected, data for 1,000 or more images can be obtained.

The local personal computing device 14 is configured to receive the signals (i.e., ECGI data) from the smart shirt 12. In some embodiments, the personal computing device 14 comprises a smart phone. Alternatively, the personal computing device 14 can comprise a tablet computer, a notebook computer, a desktop computer, or another computing device capable of receiving and transmitting the ECGI data. In some embodiments, the personal computing device 14 is configured to compress the ECGI data and periodically transmit it (e.g., over the network 18) to the remote computer 16 for processing and storage. In other embodiments, the personal computing device 14 is further configured to locally process the ECGI data. For example, one or more algorithms that execute on the personal computing device 14 can be used to reconstruct missing ECGI data that results from broken contact between electrodes 22 and the patient's skin surface. In addition, one or more algorithms can execute on the personal computing device 14 to analyze the ECGI data and detect cardiac disorders for the purpose of providing a warning to the patient and/or his physician.

The remote computer 16 can receive and process the ECGI data transmitted by the personal computing device 14. The remote server computer 16 can also comprise one or more algorithms configured to reconstruct missing ECGI data and analyze the ECGI data to detect cardiac disorders. As described below, the analysis can comprise transforming three-dimensional ECG images into two-dimensional cardiac maps through a process called cardiac cartography. With such mapping, the cardiac activity of the patient can be compared with historical cardiac data collected from the patient or from other subjects and analyzed to diagnose particular cardiac disorders. This can entail performing long-term cardiac trend analysis and integrating prior knowledge from historical databases (e.g., PhysioNet).

Figure 2:
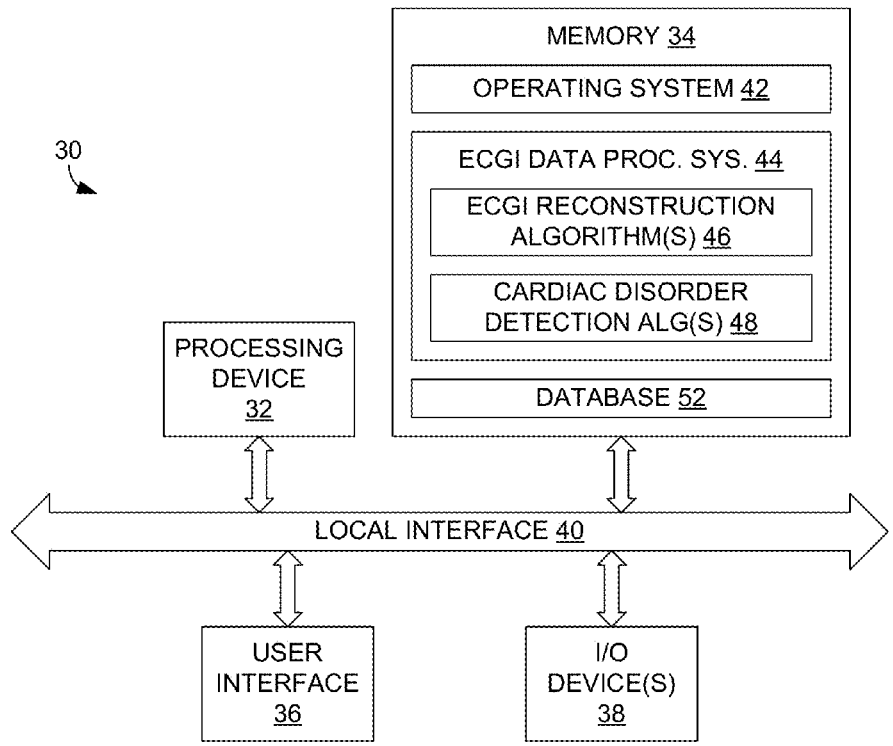
FIG. 2 is a block diagram that illustrates an example configuration for a computing device shown in FIG. 1.

FIG. 2 is a block diagram of a computing device 30, whether it be the local personal computing device 14 or the remote computer 16 shown in FIG. 1, or some other computing device that can process the ECGI data collected by the smart shirt 12. As shown in FIG. 2, the computing device 30 includes a processing device 32, memory 34, a user interface 36, and at least one I/O device 38, each of which is connected to a local interface 40. The processing device 32 can include a central processing unit (CPU) or a semiconductor-based microprocessor (in the form of a microchip). The memory 34 includes any one of or a combination of volatile memory elements (e.g., RAM) and nonvolatile memory elements (e.g., hard disk, ROM, Flash, etc.). The user interface 36 comprises the components with which a user interacts with the computing device 30, such as a keyboard, keypad, and display screen, and the I/O devices 38 are adapted to facilitate communications with other devices.

The memory 34 (a non-transitory computer-readable medium) comprises programs (logic) including an operating system 42 and an ECGI data processing system 44. In the example of FIG. 2, the data processing system 44 includes one or more ECGI reconstruction algorithms 46 that are configured to estimate data missing from the measured ECGI data and one or more cardiac disorder detection algorithms 48 that are configured to perform spatiotemporal cardiac cartography and characterization. In addition, the memory 34 comprises a database 52 that can include historical ECGI data of the patient and/or one or more other subjects.

Reconstructing Missing ECG Image Data

Figure 3:
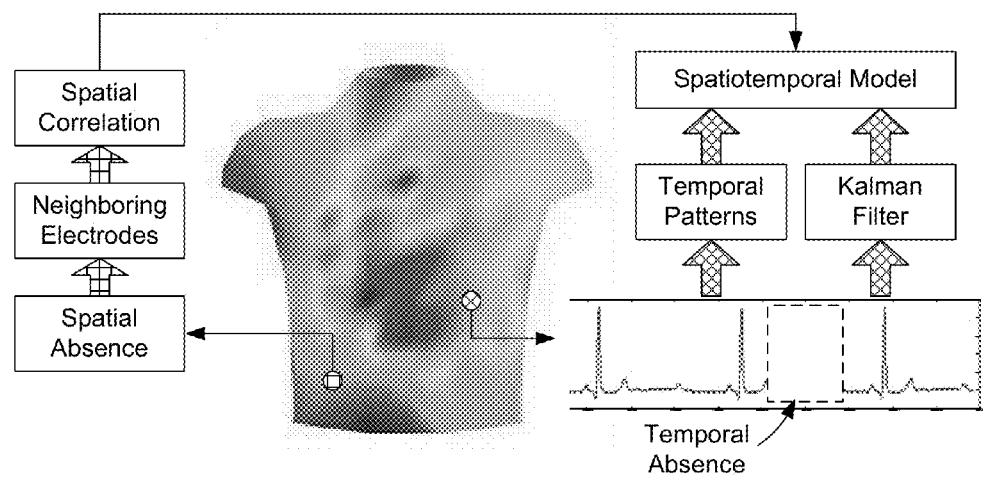
FIG. 3 is schematic diagram that illustrates a spatiotemporal estimation model for estimating missing ECG image data.

As identified above, it is desirable to optimize the wearability of the smart shirt to increase wearer comfort and enable individuals to move around and interact freely because this will increase the likelihood of such individuals actually wearing the shirt. Given the aforementioned relaxed-fit design of the shirt, however, the electrodes may intermittently lose contact with the skin surface at dynamically varying locations of the body. This loss of contact has temporal and spatial aspects. Specifically, electrodes lose contact for discrete periods of time, thereby creating a temporal absence of signals, and lose contact at discrete spatial locations of the body, thereby creating a spatial absence of signals. These absences are illustrated in FIG. 3. In some embodiments, both temporal and spatial estimation can be used to reconstruct the missing ECGI data. In particular, a spatiotemporal model can be constructed that receives as input both temporal data in the form of temporal patterns from the electrodes that have lost contact and spatial data in the form of signals from neighboring electrodes (i.e., electrodes that are positioned near the electrodes that have lost contact).

Figure 4:
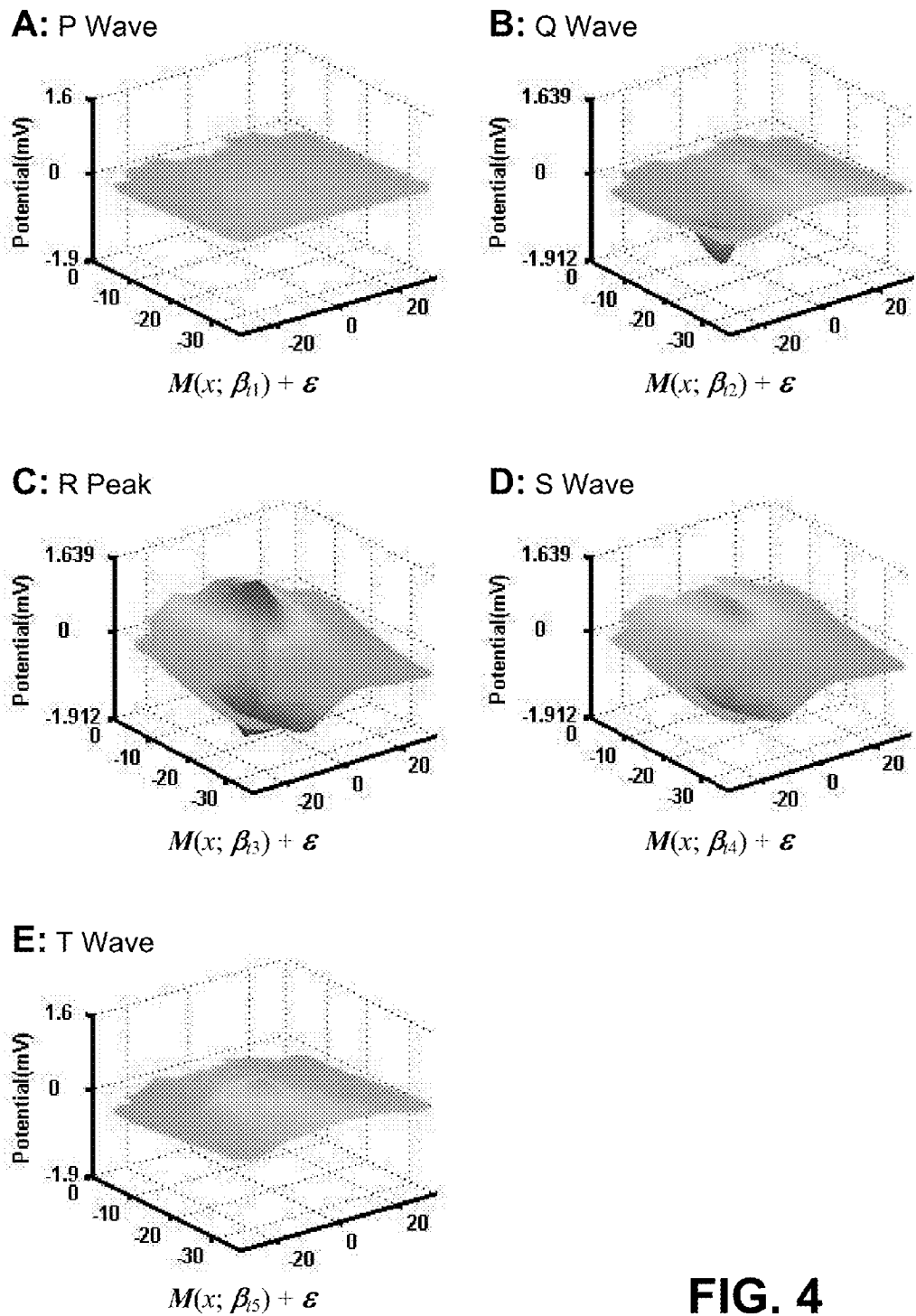
FIGS. 4A-4E are time-varying ECG imaging surfaces at the locations of the (A) P wave, (B) Q wave, (C) R peak, (D) S wave, and (E) T wave of an ECGI signal.

As can be expected, two points on an ECG image have a stronger correlation when they are closer to each other. Therefore, the spatial correlation between neighboring electrodes is valuable to estimating the spatially absent values. As shown in FIG. 4, the ECG images in the front and back of the body vary with respect to time. At a given time point, the spatial correlation in the ECG images can be captured as a model of the form:

$$Y(s) = M(s; \beta) + \varepsilon(s) = \sum_{i=1}^{N} w_i(s) f_i'(s) \beta_i + \varepsilon(s) \quad \text{[Equation 1]}$$

where Y(s) is an observation taken at location s in the body surface, $\beta_i=(\beta_{i1}, \ldots, \beta_{ip})'$ is a vector of model parameters, N is the total number of components, and $\epsilon(s)$ is Gaussian random noise. The $w_i(s)$ is a non-negative weighting kernel function, i.e., $$w_i(s) \propto |\sum_i|^{\frac{1}{2}} \exp\{-(s-\mu_i)' \sum_i^{-1} (s-\mu_i)/2.$$

The $f_i(S)=(f_{i1}(s), \ldots, f_{ip}(s))'$ is a set of known basis functions. The spatial model is designed as a locally weighted mixture of basis function regressions. For one realization of the spatiotemporal process, it can be observed that $Y=(Y(s_1), \ldots, Y(s_n))$ at locations $s_1, \ldots, s_n$. If one defines $w_i=(w_i(s_1), \ldots, w_i(s_n))$ as the vector of weights for kernel i and $X_i=\{f_{i1}(s), \ldots, f_{ip}(s)\}$ as the design matrix for the ith mixture component, the spatial model can be written as a linear regression: $Y=X\beta+\epsilon$, where $X=(diag(w_1)X_1, \ldots, diag(w_N)X_n)$ and $\beta=(\beta'_1, \ldots, \beta'_N)$. The spatially missing value $Y(\tilde{s})$ can then be estimated as $X\beta$ for the location $\tilde{s}$.

This is a kernel-weighted regression model of an ECG image. Generally, the ECG image at a given time point is non-stationary. The same Gaussian kernel or different kernels can be used for $w_i(s)$ in Equation 1. It is clear that, for the spatial model in Equation 1, an adaptive kernel function can be chosen in $w_1(s)$, which could be different from that of $w_2(s)$ to obtain a better fit to the data. Thus, kernel functions can be adaptively matched to the data for increasing the model convergence. Also, if the kernel-weighted model converges faster, a finite number of terms N would be sufficient to obtain a good approximation, which reduces the computation.

The spatial model can be augmented to include temporal components, i.e., to define the time-varying model parameters as $\beta_t=(\beta_{t1}, \ldots \beta_{tp})'$ at time t. As shown in FIG. 4, as cardiac electrical activities vary in both space and time, the ECGI surfaces $M(x;\beta_t),(x;\beta_{t+1})$ vary with respect to time. A Kalman filter (FIG. 3) can be used to establish temporal correlation to recursively estimate the state of a discrete-time controlled process, i.e., to link the parameters $\beta_t$ over time by the evolution equation:

$$\beta_t = G_t \beta_{t-1} + \omega_t, \omega_t \sim N(0, Z_t) \quad \text{[Equation 2]}$$

where $G_t$ is the evolution matrix and $\omega_t$ is the process noise with zero mean and the covariance matrix $Z_t$. Meanwhile, the spatial model at a given time is defined as:

$$Y_t = X_t \beta_t + \epsilon_t, \epsilon_t \sim N(0, V_t) \quad \text{[Equation 3]}$$

where $Y_t$ is the observed ECG image at time t and $\epsilon_t$ is the measurement noise. The Kalman filter estimates the state of model parameters $\beta_t$ at some time and then obtains feedback in the form of (noisy) measurements. The temporal predictor equation (i.e., Equation 2) is responsible for projecting forward (in time) the current state and error covariance estimates to obtain the priori estimates for the next time step. The spatial update equation (i.e., Equation 3) is responsible for providing feedback, i.e., for incorporating a new measurement of the ECG image into the priori estimate to obtain an improved posteriori estimate. After each temporal predictor and spatial update, the process is repeated with the previous posteriori estimates used to project or predict the new priori estimates. This recursive estimation using the Kalman filter makes practical implementations more feasible for modeling the time-varying model parameters. This combination of a spatial model and a Kalman-filter-type model is attractive because it can be implemented to estimate not only the spatially-temporally missing electrode values but also to predict the ECG image in the next time step.

Figure 5:
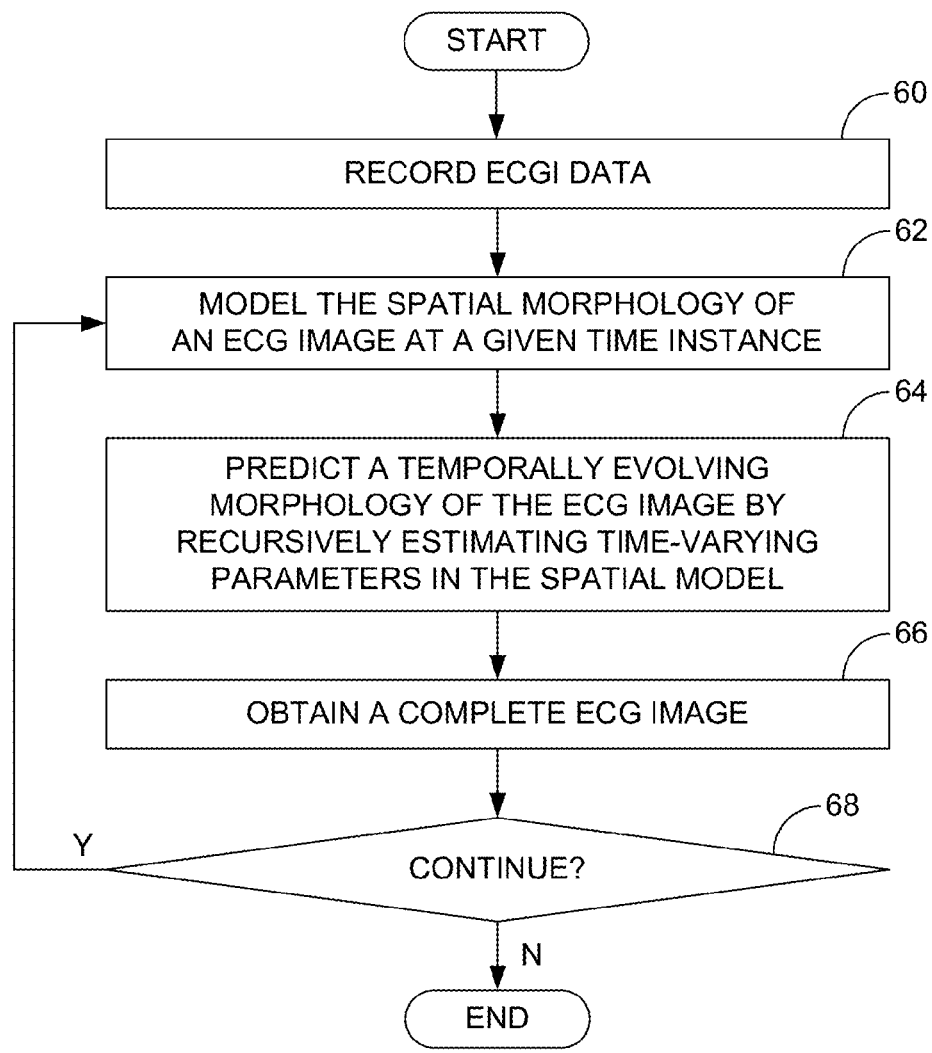
FIG. 5 is a flow diagram that illustrates an embodiment of a method reconstructing missing ECG image data.

FIG. 5 is a flow diagram that summarizes an example method for reconstructing missing ECG image data that is consistent with the above discussion. Beginning with block 60, ECGI data is recorded in the manner described above using a smart shirt. Because some of the electrodes of the shirt will not be in contact at the instant in time in which the ECGI data is recorded, spatial and temporal image data will be missing.

With reference to block 62, the spatial morphology of an ECG image recorded at the given time instance can be modeled. As described above, the spatial morphology can be modeled using a parametric model, such as a kernel-weighted regression model.

Referring next to block 64, a temporally evolving morphology of the ECG image can be predicted by recursively estimating time-varying parameters in the spatial model. When this is performed, a complete ECG image can be obtained, as indicated in block 66. At this point, flow can return to block 62 and the process can be repeated for the next ECG image, if desired (block 68).

Performing Cardiac Cartography

Once the ECGI data has been reconstructed, the data can be analyzed to detect cardiac disorders. Cardiac electrical dynamics are initiated and propagated in space and time, and these dynamics can be shifted because of the spatial localization and temporal deterioration of cardiac disorders, such as myocardial infarctions. It would therefore be desirable to have new mathematical models that identify real-time biomarkers from ECG images that are sensitive to the spatiotemporal disease process. Methods discussed below include spatial mapping, cartography, and multi-level factorial analysis. Using such methods, regions of interest can be quantified and related to spatial (i.e., anterior, posterior, inferior, superior, septal, and lateral, etc.) and temporal (i.e., ischemia, injury, necrosis) factors of cardiac disorders.

Figure 6:
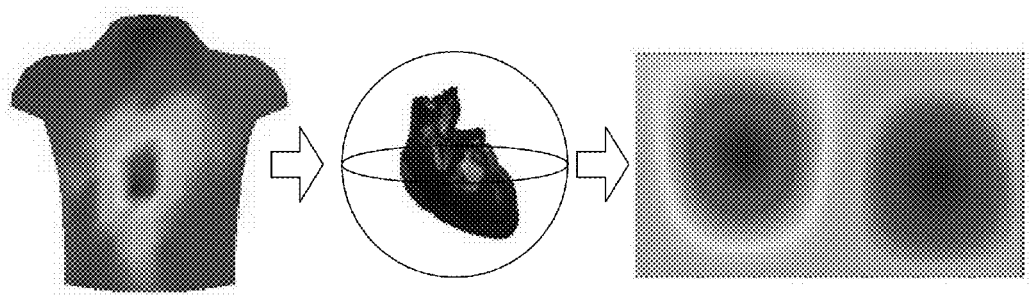
FIG. 6 is schematic diagram that illustrates a cardiac cartography process.

By using algorithms that can extract hidden knowledge in space-time ECGI data, one can study specific regions of interest that are related to spatial location and temporal progression of cardiac pathological behaviors for real-time diagnostic applications. Most existing medical devices utilize simple time-domain ECG metrics (e.g., heart rate, ST segment, QT interval) for monitoring purposes. However, cardiac electrical dynamics are initiated and propagated spatiotemporally. Such space-time activities are inevitably shifted by the spatial location and temporal progression of cardiovascular diseases. The approach described below utilizes cardiac cartography, which normalizes and maps the ECGIs onto unit spheres around the heart, as illustrated in FIG. 6. As is further depicted in FIG. 6, the unit spheres can be transformed into two-dimensional cardiac maps, in similar manner to projecting a globe's surface onto a two-dimensional plane to obtain a two-dimensional geographic map. The normalization addresses the issues of thorax inhomogeneity because of subject differences. In cardiac cartography, normalization factors can be calculated by minimizing the squared errors between the estimated ECGI datasets $\hat{E}_i(t)$ and the actual datasets $E_i(t)$ using the following equation:

$$\min \int_0^T \left[E_i(t) - \hat{E}_i(t)\right]^2 dt \text{ and } n_i = \frac{\int_0^T E_i(t) \cdot [V(t) \cdot L_i] dt}{\int_0^T [V(t) \cdot L_i]^2 dt} \quad \text{[Equation 4]}$$

where $\hat{E}_i(t) = V(t) \cdot L_i \cdot n_i$, $L_i$ is the directional vector of $i_{th}$ electrode, $n_i$ is the $i_{th}$ normalization factor, V(t) is the 3-lead VCG, and $\hat{E}_i(t)$ T is the total time. Cardiac vectors can, therefore, be normalized by multiplying with the factor n as $V_N(t) = V(t) \cdot n$, where $$n = \frac{\sum_{i=1}^{N} n_i}{N}$$

and N is the total number of electrodes. The normalized cardiac vector is then mapped onto a unit sphere as the inner product with a unit vector $u_{ij}$ on the sphere:

$$I_{ij}(t) = (V_{N_X}(t), V_{N_Y}(t), V_{N_Y}(t) \cdot (u_{x_{ij}}, u_{Y_{ij}}, u_{z_{ij}}) \quad \text{[Equation 5]}$$

Figure 7:
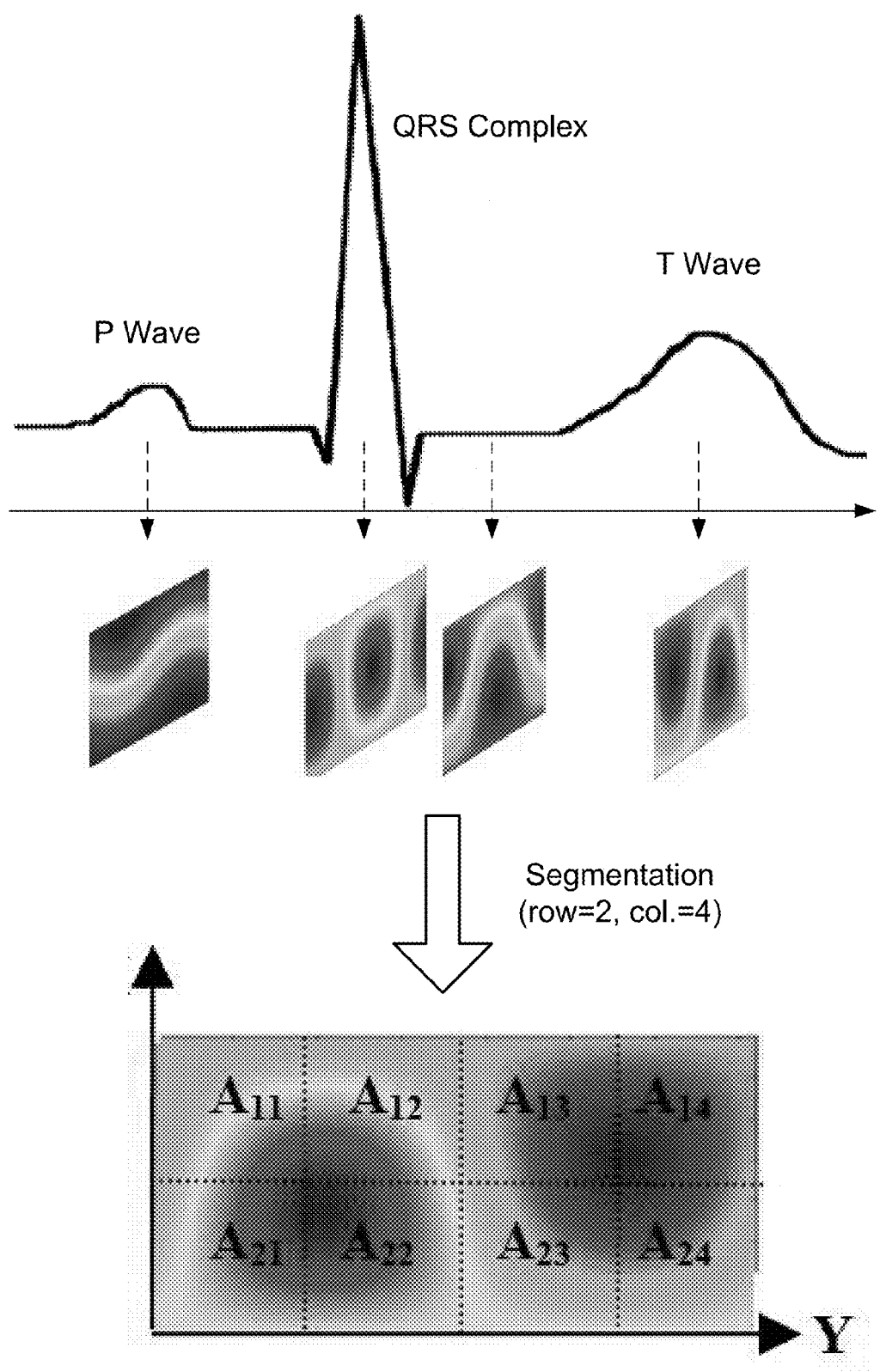
FIG. 7 is a schematic diagram that illustrates segmentation of time-varying cardiac maps resulting from cardiac cartography.

The ECG potentials on the unit sphere can then be normalized and projected on a two-dimensional surface (i.e., cartography) with map projections (e.g., cylinder, cone, plane, azimuthal projections), thereby accounting for the variation of torso morphology. As shown in FIG. 7, the two-dimensional cardiac maps vary spatiotemporally $\{V(s,t): s \in R \subset R^d, t \in T\}$, where s represents the spatial location, and t is the time.

Spatial regions of interest of the cardiac maps can be investigated during a particular time period in the time-varying cardiac cartography for purposes of identifying cardiac disorders. As shown in FIG. 7, each cardiac map at a given instant in time can be spatially partitioned into multiple uniform row-by-column sections (e.g., rows=2, 3, ..., 6 and cols=2, 3, ..., 6) so that the location of a cardiac disorder, such as a myocardial infarction, can be optimally searched. Temporally, the period $t_i \leq T \leq (t_i + \Delta t)$ will also be segmented to track the heart's sequential functioning for diagnostic clues. However, the uniform segmentation of the two-dimensional cardiac maps may roughly divide the area of myocardial infarction into several blocks (i.e., discrete bins). In an alternative approach, detection in neighboring areas can be repeatedly refined or adaptive segmentation (i.e., non-uniform) can be used to increase precision.

Figure 8:
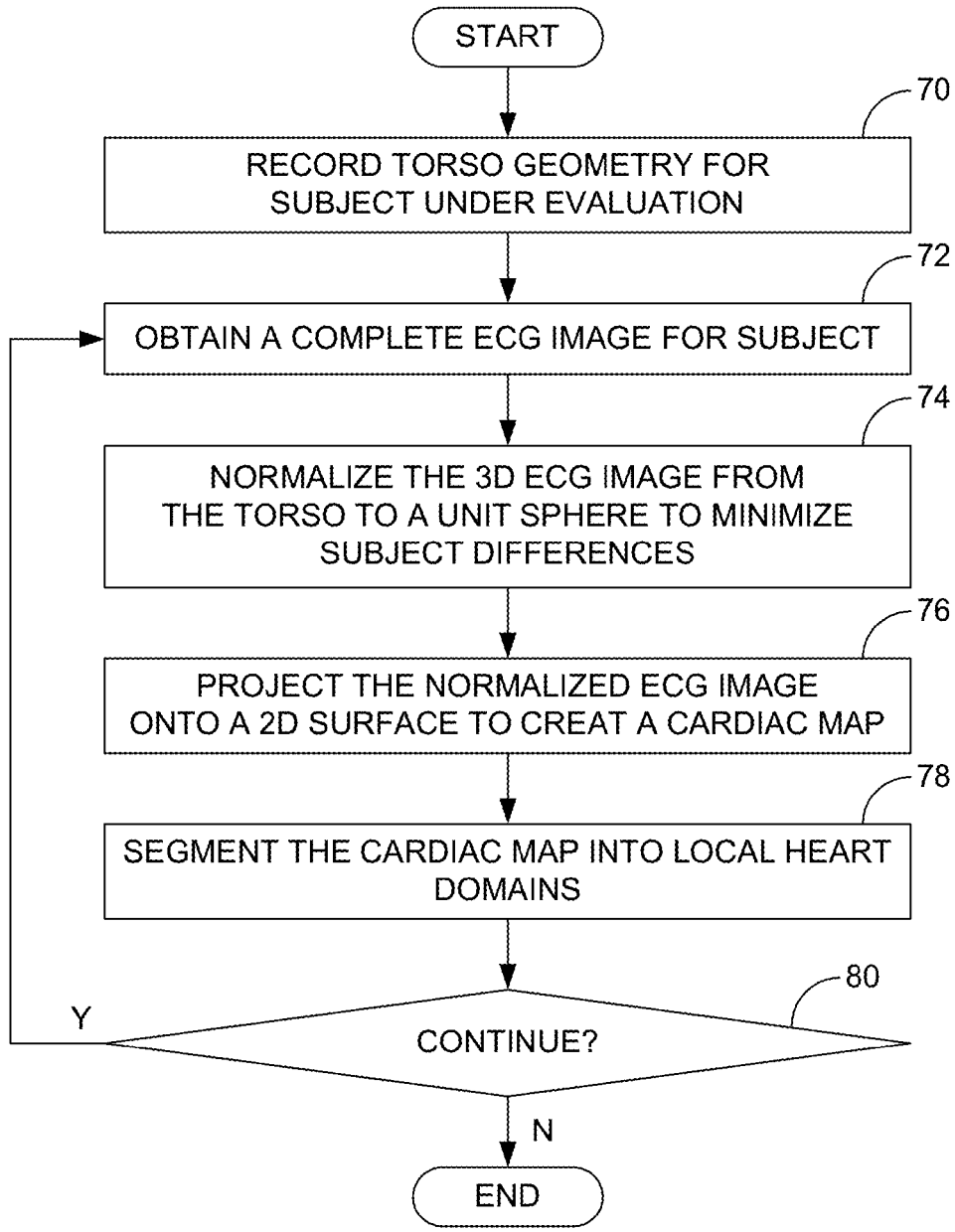
FIG. 8 is a flow diagram that illustrates an embodiment of a method for performing cardiac cartography.

FIG. 8 is a flow diagram that summarizes an example method for performing cardiac cartography that is consistent with the above discussion. Beginning with block 70, the torso geometry of the subject under evaluation is recorded. Next, a complete ECG image for the subject can be obtained, as indicated in block 72. By way of example, the ECG image is one that resulted from the image reconstruction described above.

With reference to block 74, the three-dimensional ECG image is normalized from the torso to a unit sphere to minimize the differences (size, shape, etc.) between subjects. Once this normalization has been performed, the normalized image can be projected onto a two-dimensional surface to create a cardiac map, as indicated in block 76. Again, this process is similar to projecting the surface of a globe onto a two-dimensional geographical map.

Next, the cardiac map can be segmented into one or more local heart domains, as indicated in block 78, so that the activity illustrated in the map can be associated with particular parts of the subject's heart. At this point, flow can return to block 72 and the above-described process can be performed on the next ECG image, if desired (block 80).

Determining Cardiovascular Conditions

Figure 9:
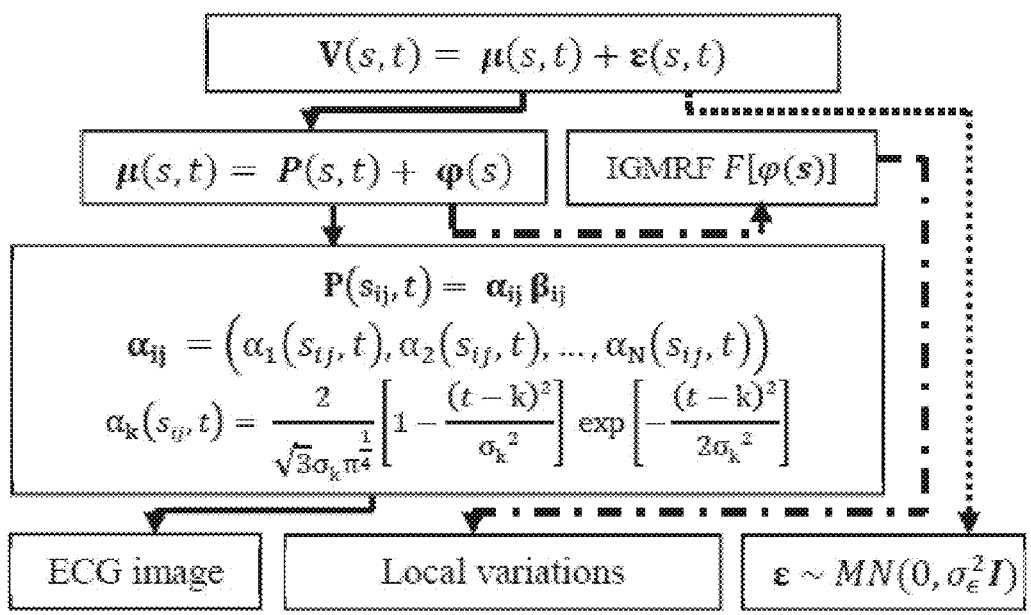
FIG. 9 is a block diagram illustrating an embodiment of a hierarchical modeling structure that can be used to detect cardiac disorders.

A Bayesian hierarchical framework can be used to predict the spatiotemporal variations of cardiac electric events accounting for uncertainties, such as respiration and muscular activities. As shown in FIG. 9, a hierarchical model separates the ECG image V(s t) into a hierarchical structure of three components:

$$V(s,t) = P(s,t) + \phi(s) + \epsilon(s,t) \quad \text{[Equation 6]}$$

where P(s,t) is the dominant morphology accounting for cardiac electric events. If the basis function $\alpha_k(s_{ij}, t)$ is chosen to be a Mexican hat function, P(s,t) at location $s_{ij}$ will be:

$$P(s_{ij}, t) = \quad \text{[Equation 7]}$$

$$\alpha_{ij} \beta_{ij} = \sum_{k=1}^{N} \beta_k \frac{2}{\sqrt{3}\, \sigma_k \pi^{\frac{1}{4}}} \left[1 - \frac{(t-k)^2}{\sigma_k^2}\right] \exp\left[-\frac{(t-k)^2}{2\sigma_k^2}\right]$$

In addition, $\phi(s)$ accounts for the local variability (e.g., brody effects, intracardiac blood mass, respiration, and muscular activities) and is modeled as:

$$f(\varphi(s)) = (2\pi)^{\frac{-(n-m)}{2}} (|Q|^*)^{\frac{1}{2}} \exp\left[-\frac{1}{2}(\varphi(s) - \mu)\right]^T Q(\varphi(s) - \mu) \quad \text{[Equation 8]}$$

using the intrinsic Gaussian Markov random field (IGMRF), where μ is the mean of $\phi(s)$, m is the dimension of null space, Q is precision matrix with rank n−m, and |Q|* denotes the product of the nonzero eigenvalues of Q. The function $\epsilon(s,t)$ is an uncorrelated random process with mean 0 and variance $\sigma_\epsilon^2$. The model can be generalized with optimal parameter settings. For example, an optimal model can be identified with the minimal hypothetic units but sufficient explanatory power. The Bayesian framework and Markov chain Monte Carlo (MCMC) simulation can be utilized to avoid the limitation of maximum likelihood based point estimate by marginalizing over the model parameters.

Figure 10:
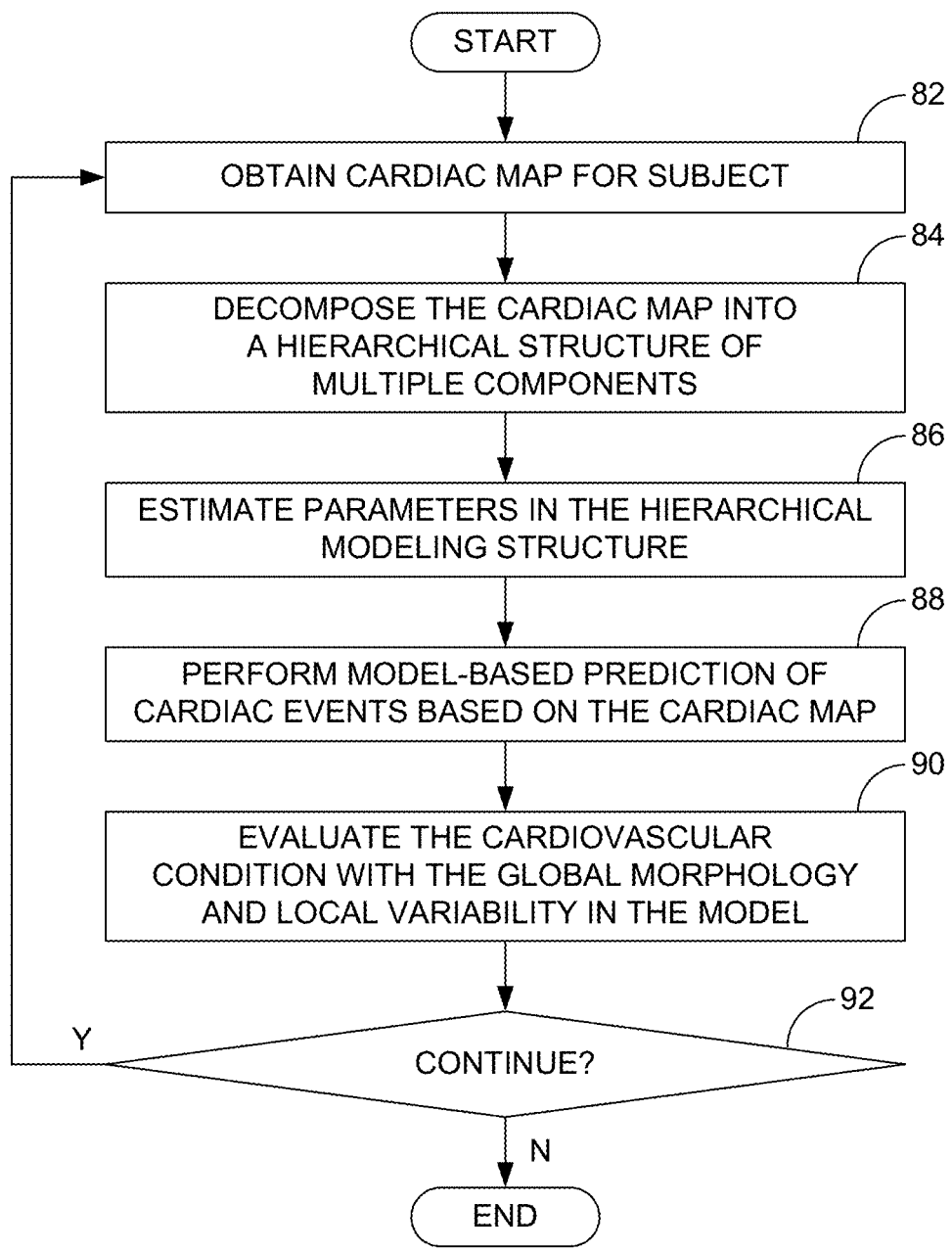
FIG. 10 is a flow diagram that illustrates an embodiment of a method for detecting cardiac disorders from cardiac maps.

FIG. 10 is a flow diagram that summarizes an example method for determining a cardiovascular condition, such as detecting a cardiac disorder from the two-dimensional cardiac maps. Beginning with block 82, a cardiac map for the subject under evaluation is obtained. Next, the cardiac map is decomposed into a hierarchical structure of multiple components, as indicated in block 84. As described above, these components can comprise global morphology, local variability, and noise.

With reference to block 86, the parameters in the hierarchical modeling structure can then be estimated. At this point, model-based prediction of cardiac events can be performed based upon the cardiac map, as indicated in block 88, and the cardiovascular condition of the subject can be evaluated with the global morphology and local variability in the model, as indicated in block 90.

Once this evaluation has been performed, flow can return to block 82 and a similar process can be performed on the next cardiac map, if desired (block 92).

The invention claimed is:

1. A method for determining a cardiovascular condition of a subject, the method comprising:
capturing a three-dimensional electrocardiography image of the subject;

generating a two-dimensional cardiac map from the electrocardiography image; and processing the cardiac map to determine the cardiovascular condition of the subject.

2. The method of claim 1, wherein capturing a three-dimensional electrocardiography image of a subject comprises capturing a three-dimensional electrocardiography image of a subject using a smart shirt worn by the subject, the smart shirt comprising hundreds of electrodes adapted to measure electrical potentials around the subject's torso.

3. The method of claim 2, wherein the smart shirt has a relaxed fit so that not every electrode is in contact with the subject's skin at all times when the shirt is worn.

4. The method of claim 3, further comprising estimating missing data that results from electrodes losing contact with the subject's skin.

5. The method of claim 4, wherein estimating missing data comprises generating a spatial model that models a spatial morphology of the electrocardiography image.

6. The method of claim 5, wherein estimating missing data further comprises predicting a temporally evolving morphology of the electrocardiography image by recursively estimating time-varying parameters in the spatial model.

7. The method of claim 1, wherein generating a two-dimensional cardiac map comprises normalizing the electrocardiography image onto a unit sphere.

8. The method of claim 7, wherein generating a two-dimensional cardiac map further comprises projecting the normalized electrocardiography image onto a two-dimensional surface to create the cardiac map.

9. The method of claim 1, wherein processing the cardiac maps comprises decomposing the cardiac map into a hierarchical modeling structure.

10. The method of claim 9, wherein the hierarchical modeling structure comprises a global morphology, a local variability, and noise.

11. The method of claim 10, wherein processing the cardiac maps further comprises estimating parameters in the hierarchical modeling structure.

12. The method of claim 11, wherein processing the cardiac maps further comprises evaluating the cardiovascular condition of the subject with the global morphology and the local variability.

13. A non-transitory computer-readable medium that stores an electrocardiography data processing system comprising:

logic configured to receive a three-dimensional electrocardiography image of a subject;

logic configured to generate a two-dimensional cardiac map from the electrocardiography image; and logic configured to process the cardiac map to determine the cardiovascular condition of the subject.

14. The computer-readable medium of claim 13, further comprising logic configured to estimate missing data that results from electrodes losing contact with the subject's skin.

15. The computer-readable medium of claim 14, wherein the logic configured to estimate missing data comprises logic configured to generate a spatial model that models a spatial morphology of the electrocardiography image and predict a temporally evolving morphology of the electrocardiography image by recursively estimating time-varying parameters in the spatial model.

16. The computer-readable medium of claim 13, wherein the logic configured to generate a two-dimensional cardiac map is configured to normalize the electrocardiography image onto a unit sphere and project the normalized electrocardiography image onto a two-dimensional surface to create the cardiac map.

17. The computer-readable medium of claim 13, wherein the logic configured to process the cardiac map is configured to decompose the cardiac map into a hierarchical modeling structure including a global morphology, a local variability, and noise, estimate parameters in the hierarchical modeling structure, and evaluate the cardiovascular condition of the subject with the global morphology and the local variability.

* * * * *